US012560593B2

(12) United States Patent
Miura et al.

(10) Patent No.: US 12,560,593 B2
(45) Date of Patent: Feb. 24, 2026

(54) ANALYSIS DEVICE AND ANALYSIS METHOD

(71) Applicant: FUJIFILM Corporation, Tokyo (JP)

(72) Inventors: Yoshinobu Miura, Kanagawa (JP); Yuki Arai, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 532 days.

(21) Appl. No.: 18/185,450

(22) Filed: Mar. 17, 2023

(65) Prior Publication Data

US 2023/0324372 A1     Oct. 12, 2023

(30) Foreign Application Priority Data

Mar. 22, 2022     (JP) ................................. 2022-046015

(51) Int. Cl.
 *G01N 33/52*          (2006.01)
 *B01L 3/00*           (2006.01)
 *G01N 21/78*          (2006.01)

(52) U.S. Cl.
 CPC .......... *G01N 33/525* (2013.01); *B01L 3/5023* (2013.01); *G01N 21/78* (2013.01);
 (Continued)

(58) Field of Classification Search
 CPC .... G01N 33/525; G01N 21/78; G01N 21/274; B01L 3/5023; B01L 2200/16;
 (Continued)

(56) References Cited

U.S. PATENT DOCUMENTS

2006/0153738 A1     7/2006  Tanji
2009/0093968 A1     4/2009  Kawamata et al.
             (Continued)

FOREIGN PATENT DOCUMENTS

JP              5-23132 U        3/1993
JP         2004-132706 A         4/2004
             (Continued)

OTHER PUBLICATIONS

English Translation JP2012211782A (Year: 2025).*
Japanese Office Action for corresponding Japanese Application No. 2022-046015, dated Aug. 12, 2025, with English translation.

*Primary Examiner* — Jennifer Wecker
*Assistant Examiner* — Steven Ray Castaneda
(74) *Attorney, Agent, or Firm* — Birch, Stewart, Kolasch & Birch, LLP

(57)     ABSTRACT

An analysis device uses an analysis chip having two regions of a first region, which has a reagent reacting with a substance to be tested, and a second region, which does not have the reagent, and includes a first light source that irradiates the first region with light from a first surface side, a second light source that irradiates the second region with light from a second surface side, a first photodetector that detects first output light and that outputs a first detection signal corresponding to the first output light, a second photodetector that detects second output light and that outputs a second detection signal corresponding to the second output light, and a processor that acquires the first detection signal, acquires the second detection signal, and corrects the first detection signal with the second detection signal to derive a concentration of the substance to be tested.

9 Claims, 5 Drawing Sheets

(52) U.S. Cl.
CPC ... *B01L 2200/16* (2013.01); *B01L 2300/0654*
(2013.01); *B01L 2300/069* (2013.01); *B01L*
*2300/0803* (2013.01)

(58) Field of Classification Search
CPC ....... B01L 2300/0654; B01L 2300/069; B01L
2300/0803
See application file for complete search history.

(56) References Cited

U.S. PATENT DOCUMENTS

| | | | |
|---|---|---|---|
| 2013/0171675 A1 | 7/2013 | Tsukamoto et al. | |
| 2017/0268989 A1 | 9/2017 | Aubert et al. | |

FOREIGN PATENT DOCUMENTS

| | | | |
|---|---|---|---|
| JP | 2010-19610 A | 1/2010 | |
| JP | 2012-211782 A | 11/2012 | |
| WO | WO 2007/007849 A1 | 1/2007 | |
| WO | WO 2012/043444 A1 | 4/2012 | |

* cited by examiner

FIG. 5

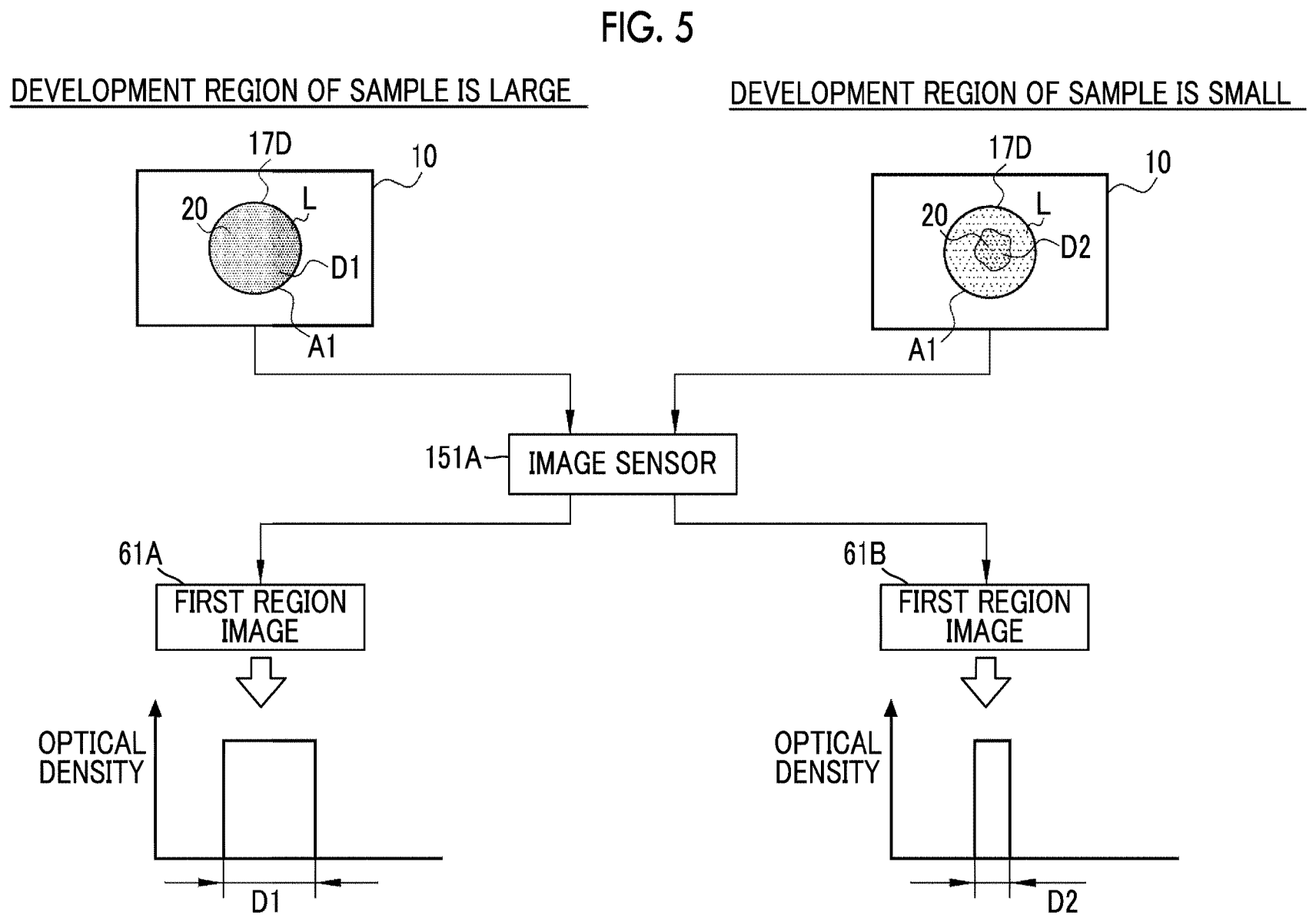

DEVELOPMENT REGION OF SAMPLE IS LARGE

DEVELOPMENT REGION OF SAMPLE IS SMALL

IMAGE SENSOR

FIRST REGION IMAGE

FIRST REGION IMAGE

OPTICAL DENSITY

OPTICAL DENSITY

ANALYSIS DEVICE AND ANALYSIS METHOD

CROSS REFERENCE TO RELATED APPLICATIONS

This application claims priority from Japanese Application No. 2022-046015, filed on Mar. 22, 2022, the entire disclosure of which is incorporated herein by reference.

BACKGROUND

1. Technical Field

The present disclosure relates to an analysis device and an analysis method.

2. Related Art

In point-of-care testing (POCT), an analysis device is known which performs sample analysis, such as the measurement of the concentration of a substance to be tested included in a sample. A blood test is given as an example of the sample analysis. In the blood test, there is a device that measures the concentration of the substance to be tested included in blood. There is an increasing demand for shortening a measurement time and reducing the size of the device. In order to meet the demand, an analysis chip may be used to omit a pretreatment step such as the centrifugation of blood plasma or the like from whole blood. For example, JP2012-211782A discloses an analysis device which optically performs a blood test using an analysis chip comprising a development layer in which blood is developed as a sample and a reaction layer which has a reagent. The analysis device disclosed in JP2012-211782A comprises a first photodetector that detects reflected light from the analysis chip and a second photodetector that detects transmitted light from the analysis chip.

In a case in which the above-described analysis chip is used and the sample is instilled into the development layer of the analysis chip, the sample is developed in the development layer. In a case in which the sample reaches the reaction layer, the substance to be tested in the sample reacts with the reagent in the reaction layer to generate a reactant that develops a color. The analysis device disclosed in JP2012-211782A can measure the concentration of the substance to be tested in the sample by irradiating the reaction layer, in which the sample and the reagent react with each other, with detection light, which includes light having a wavelength absorbed by the reactant that develops a color, from a light source and acquiring a detection signal corresponding to the reflected light from the reaction layer.

SUMMARY

However, since the sample developed in the analysis chip includes various substances other than the substance to be tested, the detection signal corresponding to the reflected light from the reaction layer in which the sample and the reagent react with each other may include, as noise, a signal caused by a substance that does not react with the reagent. Therefore, the analysis device disclosed in JP2012-211782A that acquires only the detection signal from the reaction layer has room for improvement in order to measure the concentration with high accuracy.

The technology of the present disclosure provides an analysis device and an analysis method that can measure a concentration of a substance to be tested in a sample with higher accuracy than that in the related art in a case in which the sample is analyzed using an analysis chip.

According to one aspect of the present disclosure, there is provided an analysis device that analyzes a sample including a substance to be tested and that uses an analysis chip that has two regions of a first region, which has a reagent reacting with the substance to be tested, and a second region, which does not have the reagent, and has a first surface in which the first region is provided and a second surface which is opposite to the first surface and in which the second region is provided. The analysis device comprises: a first light source that irradiates the first region of the analysis chip with light from a first surface side; a second light source that irradiates the second region of the analysis chip with light from a second surface side; a first photodetector that detects first output light which is output from the first region in a case in which the first light source irradiates the analysis chip with the light and that outputs a first detection signal corresponding to the first output light; a second photodetector that detects second output light which is output from the second region in a case in which the second light source irradiates the analysis chip with the light and that outputs a second detection signal corresponding to the second output light; and a processor that acquires the first detection signal from the first photodetector, acquires the second detection signal from the second photodetector, and corrects the first detection signal with the second detection signal to derive a concentration of the substance to be tested.

In the analysis device according to the above-described aspect, the first photodetector and the second photodetector may detect the light at different times.

In addition, in the analysis device according to the above-described aspect, the first photodetector may be an image sensor that has an imaging surface in which a plurality of light-receiving elements are two-dimensionally arranged and that is capable of imaging the first region and outputting a first region image obtained by imaging the first region as the first detection signal, and the processor may identify a development region in which the sample has been developed in the first region on the basis of the first region image and correct the first detection signal according to the development region.

Further, in the analysis device according to the above-described aspect, the second photodetector may be an image sensor that has an imaging surface in which a plurality of light-receiving elements are two-dimensionally arranged and is capable of imaging the second region and outputting a second region image obtained by imaging the second region as the second detection signal, and the processor may identify a development region in which the sample has been developed in the second region on the basis of the second region image and correct the second detection signal according to the development region.

Furthermore, in the analysis device according to the above-described aspect, a wavelength range of the light emitted from the first light source and from the second light source includes light in a specific wavelength range that is determined according to at least one of the substance to be tested or the reagent.

Moreover, in the analysis device according to the above-described aspect, the first light source and the second light source may be capable of emitting light in a plurality of different wavelength ranges as the light in the specific wavelength range.

Furthermore, in the analysis device according to the above-described aspect, the reagent may be a dry reagent.

Moreover, in the analysis device according to the above-described aspect, the sample may be whole blood, and the substance to be tested may be a specific substance included in blood plasma or in blood serum.

According to another aspect of the present disclosure, there is provided an analysis method for analyzing a sample including a substance to be tested. An analysis chip, which has two regions of a first region and a second region and has a first surface and a second surface opposite to the first surface, is used, the first region has a reagent reacting with the substance to be tested, the second region does not have the reagent, the first region is provided in the first surface, and the second region is provided in the second surface. The analysis method comprises: a step of irradiating the first region of the analysis chip with light from a first surface side with a first light source; a step of irradiating the second region of the analysis chip with light from a second surface side with a second light source; a step of causing a first photodetector to detect first output light which is output from the first region in a case in which the first light source irradiates the analysis chip with the light and acquiring a first detection signal output by the first photodetector; a step of causing a second photodetector to detect second output light which is output from the second region in a case in which the second light source irradiates the analysis chip with the light and acquiring a second detection signal output by the second photodetector; and a step of acquiring the first detection signal, acquiring the second detection signal, and correcting the first detection signal with the second detection signal to derive a concentration of the substance to be tested.

According to the technology of the present disclosure, it is possible to measure the concentration of a substance to be tested in a sample with higher accuracy than in the related art in a case in which the sample is analyzed using an analysis chip.

BRIEF DESCRIPTION OF THE DRAWINGS

FIG. 5 is a diagram in a case in which an image sensor is used.

DETAILED DESCRIPTION

Hereinafter, preferred embodiments of the invention will be described with reference to the drawings.

First Embodiment

Figure 1:
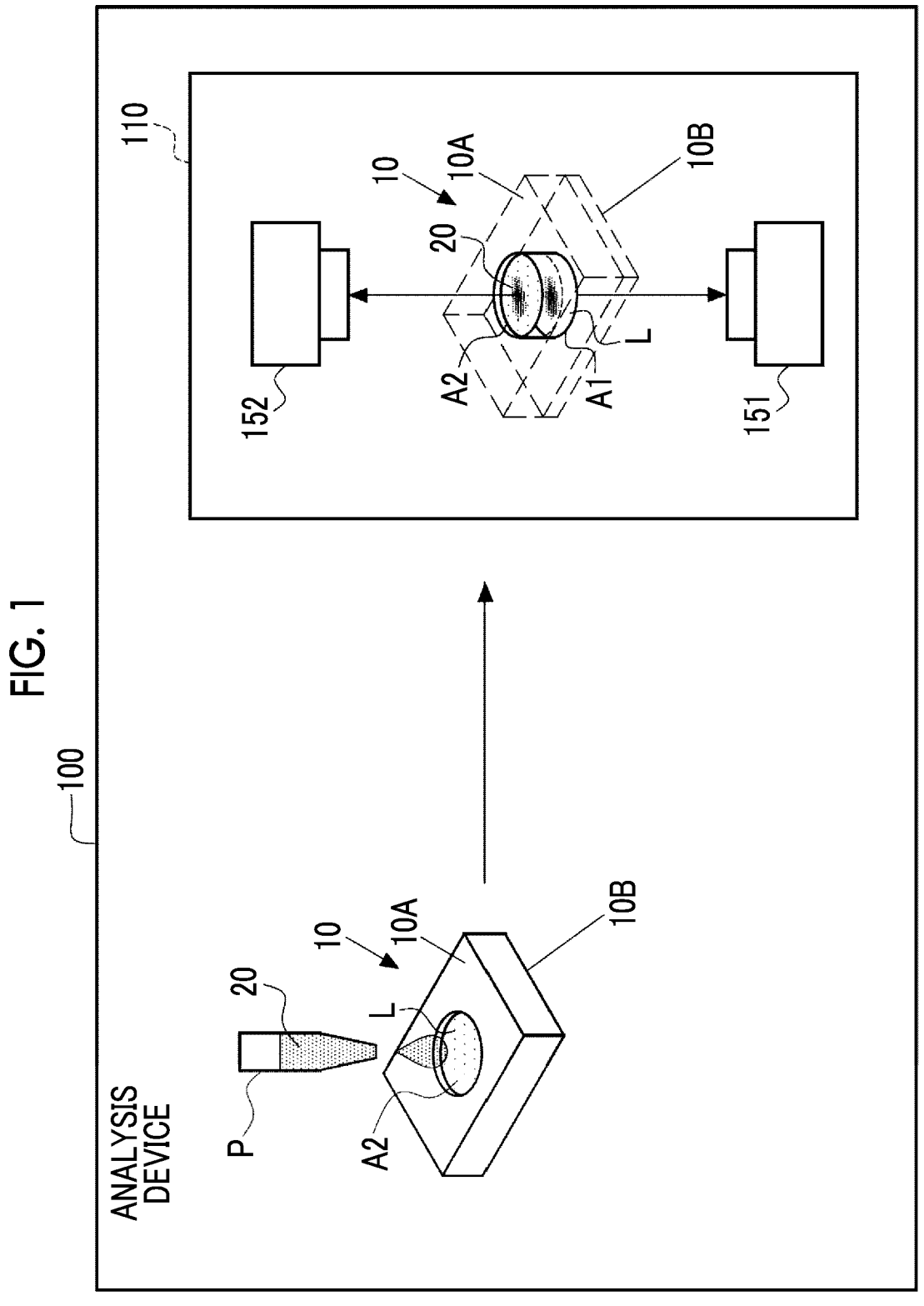
FIG. 1 is a schematic diagram illustrating an analysis device and an analysis method.

An analysis device 100 according to a first embodiment of the present disclosure illustrated in FIG. 1 is an example of an analysis device that analyzes a sample 20 and measures the concentration of a substance to be tested which is included in the sample 20, using an analysis chip 10. Specifically, the analysis device 100 according to this example uses blood as the sample 20 and optically measures the concentration of the substance to be tested which is included in the blood. More specifically, the sample 20 is, for example, whole blood.

The analysis device 100 includes a dispensing mechanism P and a measurement unit 110. The dispensing mechanism P instills the sample 20 into the analysis chip 10. The measurement unit 110 performs a process of measuring the concentration of the substance to be tested, using the analysis chip 10 into which the sample 20 has already been instilled. The analysis chip 10 is loaded on the measurement unit 110.

In addition, in a case in which it is necessary to wait for a time after the instillation of the sample 20 to perform the measurement, the sample 20 may be instilled before the chip is loaded on the measurement unit 110. The time when the sample is instilled is appropriately determined depending on the type of the sample 20 or the like.

The analysis chip 10 has a first region A1 that has a reagent L and a second region A2 that does not have the reagent L. The analysis chip 10 has, for example, a flat plate shape and has a first surface 10A and a second surface 10B that is opposite to the first surface 10A. In the analysis chip 10, the second region A2 is provided in the first surface 10A, and the first region A1 is provided in the second surface 10B. The reagent L reacts with the substance to be tested to generate a substance that develops a specific color. Hereinafter, the substance that develops a color via this reaction is referred to as a reactant. For example, a dry reagent that is in a dry state at least in a case of shipment is used as the reagent L. The sample 20 is instilled into each of the first region A1 and the second region A2.

The measurement unit 110 acquires detection signals indicating the optical densities of the first region A1 and the second region A2 using the analysis chip 10 into which the sample 20 has already been instilled. The measurement unit 110 derives the concentration of the substance to be tested which is included in the sample 20 on the basis of the two acquired detection signals. The measurement unit 110 is provided with a first photodetector 151 and a second photodetector 152. The first photodetector 151 detects first output light that is output from the first region A1 and outputs a first detection signal corresponding to the first output light, which will be described below. The second photodetector 152 detects second output light that is output from the second region A2 and outputs a second detection signal corresponding to the second output light.

Figure 2:
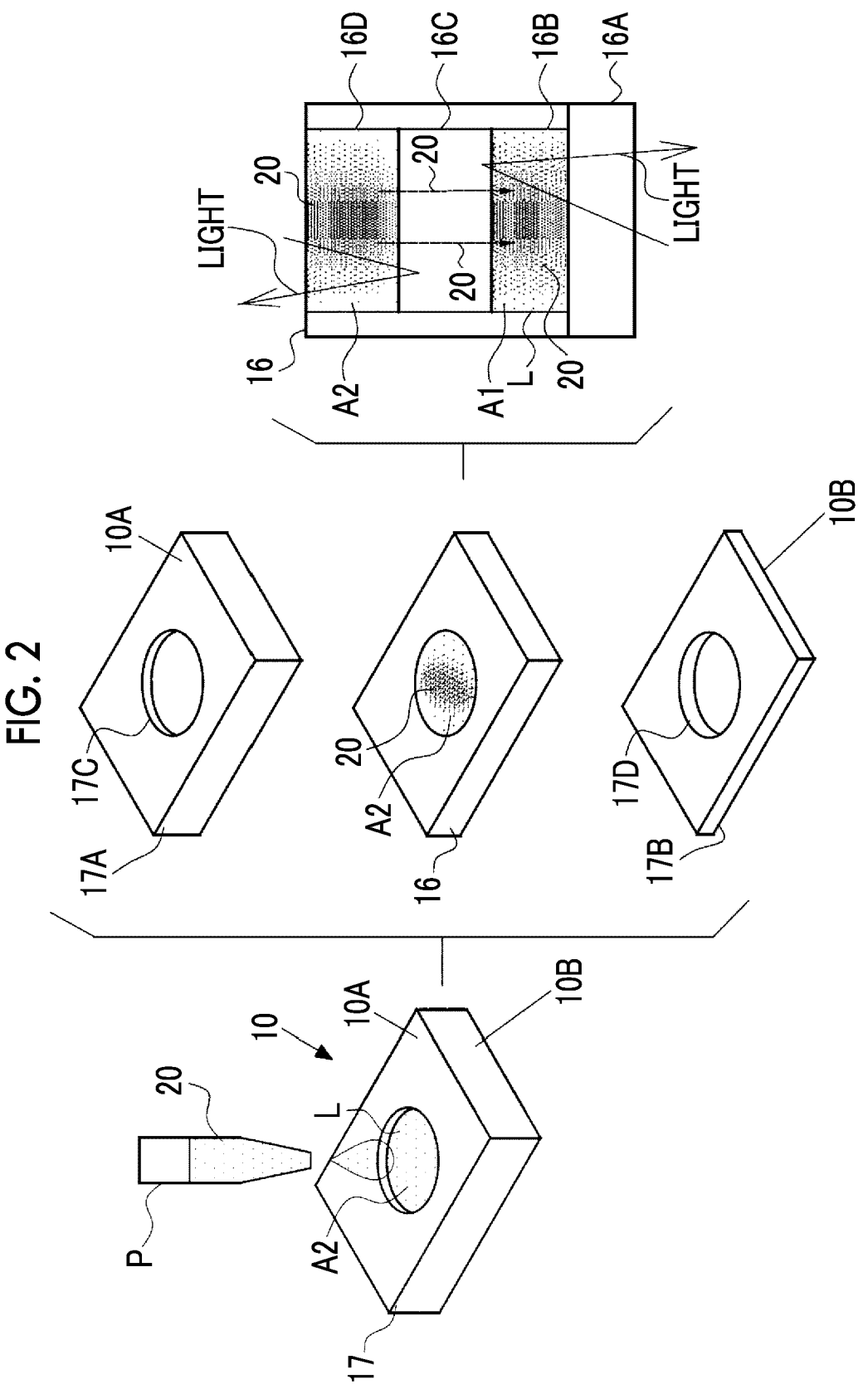
FIG. 2 is a diagram illustrating a configuration of an analysis chip.

FIG. 2 illustrates a configuration of the analysis chip 10. As illustrated in FIG. 2, the analysis chip 10 comprises a carrier 16 into which the sample 20 is instilled and a case 17 which accommodates the carrier 16. The case 17 includes a first case 17A and a second case 17B and accommodates the carrier 16 such that the carrier 16 is interposed between the first case 17A and the second case 17B in a vertical direction in FIG. 2. An opening 17C through which at least a portion of the second region A2 is exposed to the outside is formed in the first case 17A, and an opening 17D through which at least a portion of the first region A1 is exposed to the outside is formed in the second case 17B. The opening 17C functions as a drip opening for instilling the sample 20 into the carrier 16 in the second region A2. In addition, the opening 17C functions as an opening for irradiating the second region A2 with light and taking out output light from the second region A2. Similarly, the opening 17D functions as a drip opening for instilling the sample 20 into the carrier 16 in the first region A1. In addition, the opening 17D functions as an opening for irradiating the first region A1 with light and taking out output light from the first region A1.

The carrier 16 comprises a transparent support 16A, a reaction layer 16B, a reflective layer 16C, and a development layer 16D. The reaction layer 16B, the reflective layer 16C, and the development layer 16D are stacked in this order from the transparent support 16A. In the carrier 16, the development layer 16D is disposed closest to the first case 17A (that is, the first surface 10A), and a portion of the development layer 16D is exposed to the outside of the case 17 through the opening 17C. Further, a transparent support 16A is disposed closest to the second case 17B (that is, the second surface 10B). A portion of the transparent support 16A is exposed to the outside of the case 17 through the opening 17D. In this example, the development layer 16D of the carrier 16 is the second region A2, and the reaction layer 16B is the first region A1.

The transparent support 16A transmits light incident from the opening 17D to the reaction layer 16B. The transparent support 16A may not be a completely transparent support having a transmittance of 100% and may transmit at least a portion of the incident light.

Each of the reaction layer 16B, the reflective layer 16C, and the development layer 16D is made of a porous material and has a developing force for developing a liquid with a capillary force and a holding force for holding the developed liquid.

In a case in which the sample 20 is instilled through the opening 17C, the development layer 16D develops the sample 20 in an in-plane direction of the development layer 16D and in a direction toward the reaction layer 16B using the capillary force. A portion of the sample 20 stays in the development layer 16D, and a portion thereof reaches the reaction layer 16B.

The reflective layer 16C is a layer that reflects the incident light. A portion of the light incident from the opening 17C is transmitted through the development layer 16D and is incident on the reflective layer 16C. The reflective layer 16C reflects the light incident from the development layer 16D to be output from the opening 17C. On the other hand, a portion of the light incident from the opening 17D is transmitted through the transparent support 16A and is incident on the reflective layer 16C. The reflective layer 16C reflects the light incident from the transparent support 16A to be output from the opening 17D.

The reaction layer 16B is a layer which can hold the reagent L and in which the reagent L can react with the sample 20 developed from the development layer 16D. In the reaction layer 16B, for example, the reagent L is fixed in a region corresponding to the opening 17D. In this example, the opening 17D has a circular shape, and the region in which the reagent L is fixed is also a circular region that has the same diameter as the opening 17D. Further, the sizes and positions of the opening 17D and the region in which the reagent L is fixed are matched with each other such that the entire region in which the reagent L is fixed is exposed to the outside through the opening 17D.

Since the development layer 16D is a region that does not have the reagent L, it functions as the second region A2 as described above. Only the sample 20 is developed in the development layer 16D. In this example, light that is incident on the development layer 16D from the opening 17C is the second output light. A portion of the second output light is absorbed by the development layer 16D, a portion thereof is reflected by the development layer 16D, and a portion thereof is transmitted through the development layer 16D. The light transmitted through the development layer 16D is reflected by the reflective layer 16C and is incident on the development layer 16D again. The light that is transmitted through the development layer 16D and output from the opening 17C is the second output light that is output from the second region A2.

On the other hand, since the reaction layer 16B is a region having the reagent L, it functions as the first region A1 as described above. The reaction layer 16B holds the reagent L, and the sample 20 is developed in the reaction layer 16B. Therefore, in the reaction layer 16B, the reagent L and the substance to be tested included in the sample 20 react with each other. In this example, light that is transmitted through the transparent support 16A from the opening 17D and that is incident on the reaction layer 16B is the first output light. A portion of the first output light is absorbed by the reaction layer 16B, a portion thereof is reflected by the reaction layer 16B, and a portion thereof is transmitted through the reaction layer 16B. The light transmitted through the reaction layer 16B is reflected by the reflective layer 16C and is incident on the reaction layer 16B again. The light that is transmitted through the reaction layer 16B and that is output from the opening 17D is the first output light that is output from the first region A1.

Figure 3:
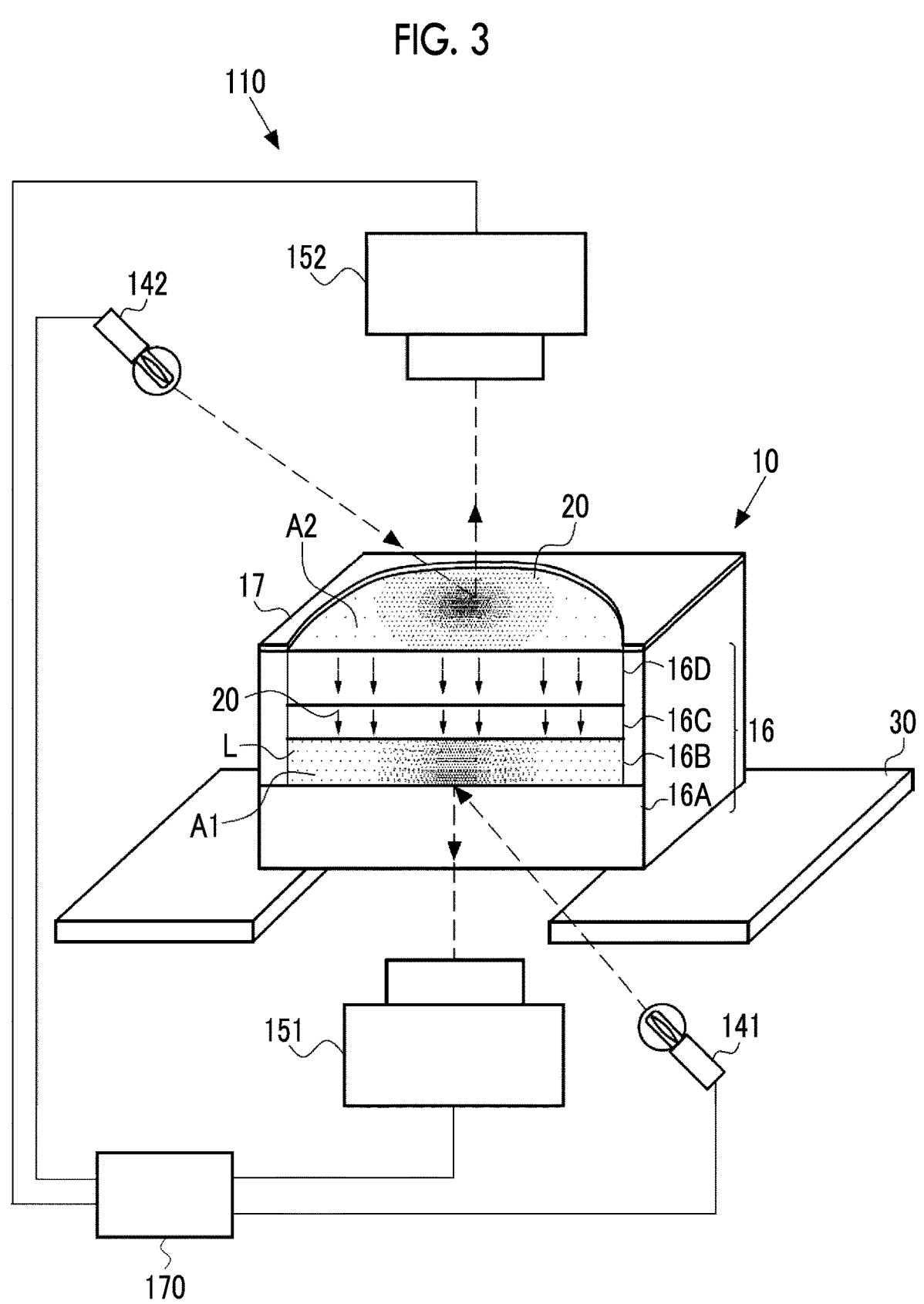
FIG. 3 is a schematic diagram illustrating a configuration of a measurement unit of the analysis device.

FIG. 3 illustrates a configuration of the measurement unit 110 of the analysis device 100. The measurement unit 110 comprises a loading unit 30, a first light source 141, a second light source 142, a first photodetector 151, a second photodetector 152, and a processor 170. The loading unit 30 holds a loaded analysis chip to be measured. In FIG. 3, in the analysis chip 10, while the configuration of the carrier 16 is clearly illustrated, the case 17 is partially omitted and is schematically illustrated.

The first light source 141 irradiates the first region A1 (that is, the reaction layer 16B) of the analysis chip 10 with light. Specifically, the first light source 141 irradiates the first region A1 with light through the opening 17D of the analysis chip 10. The wavelength range of light is determined according to at least one of the substance to be tested, the reagent, or the like. In this example, as described above, a reactant that develops a specific color is generated by the reaction between the substance to be tested and the reagent L. The light emitted by the first light source 141 is detection light for detecting whether or not the reactant is generated. Therefore, the wavelength range of the light emitted by the first light source 141 is determined according to the color developed by the reactant. Since the reactant is generated by the reaction between the substance to be tested and the reagent L, finally, the wavelength range of the light emitted by the first light source 141 is determined according to at least one of the substance to be tested or the reagent L. Hereinafter, the light emitted by the first light source 141 is referred to as first detection light. The first detection light according to this example is, for example, light that includes a wavelength range absorbed by the reactant in order to detect the reactant.

In particular, it is preferable that the wavelength range of the first detection light is limited to the wavelength range absorbed by the reactant. This is because the contrast of the optical density of light in this wavelength range is highest depending on whether the reactant is present or absent. For example, a light source, such as a light emitting diode (LED), an organic electro-luminescence (EL) device, or a semiconductor laser, is used as the first light source 141. In addition, a light source that emits light in a relatively broad wavelength range, such as a white light source, may be combined with a bandpass filter that transmits only a specific wavelength range to generate detection light that is limited to a specific wavelength range. In addition, one first light source 141 is illustrated in this example. However, a plurality of first light sources 141 may be provided as necessary.

The second light source 142 irradiates the second region A2 (that is, the development layer 16D) of the analysis chip 10 with light. Specifically, the second light source 142 irradiates the second region A2 with light through the opening 17C of the analysis chip 10. The wavelength range of the light emitted by the second light source 142 is substantially the same as that of the first detection light from the first light source 141. The light emitted by the second light source 142 is referred to as second detection light. In addition, since the second light source 142 is a light source different from the first light source 141, there is a difference therebetween caused by individual differences. Therefore, the wavelength ranges of the first detection light and the second detection light may be strictly different from each other.

The first photodetector 151 detects the output light that is output from the first region A1 in a case in which the first region A1 of the analysis chip 10 is irradiated with the first detection light.

In a case in which the first light source 141 irradiates the first region A1 with the first detection light, the first detection light is transmitted through the transparent support 16A and is incident on the reaction layer 16B as described above. In the reaction layer 16B, a reactant that develops a specific color is generated by the reaction between the reagent L and the substance to be tested. A portion of the first detection light incident on the reaction layer 16B is absorbed by the reactant. In addition, in some cases, a portion of the first detection light is reflected by the reaction layer 16B. The first detection light transmitted through the reaction layer 16B is reflected by the reflective layer 16C and is incident on the reaction layer 16B again. As described above, a portion of the first detection light incident on the first region A1 is reflected by the reaction layer 16B, which is the first region A1, and by the reflective layer 16C, and the reflected light is output from the opening 17D. The reflected light that is output from the first region A1 through the opening 17D is an example of the output light and is hereinafter referred to as first output light.

On the other hand, in a case in which the second light source 142 irradiates the second region A2 with the second detection light, the second detection light is incident on the development layer 16D as described above. A portion of the second detection light incident on the development layer 16D is absorbed or reflected by the development layer 16D, and a portion thereof is transmitted through the development layer 16D. The light transmitted through the development layer 16D is reflected by the reflective layer 16C and is incident on the development layer 16D again. As described above, a portion of the second detection light incident on the second region A2 is reflected by the development layer 16D, which is the second region A2, and by the reflective layer 16C, and the reflected light is output from the opening 17C. The reflected light output from the second region A2 through the opening 17C is an example of output light and is hereinafter referred to as second output light.

The first photodetector 151 outputs a first detection signal corresponding to the first output light in a case in which it detects the first output light from the first region A1. Meanwhile, the second photodetector 152 outputs a second detection signal corresponding to the second output light in a case in which it detects the second output light from the second region A2. The first photodetector 151 outputs the first detection signal to the processor 170, and the second photodetector 152 outputs the second detection signal to the processor 170. The first photodetector 151 and the second photodetector 152 are, for example, light-receiving elements, such as photodiodes, that output a detection signal corresponding to the amount of light. Each of the first photodetector 151 and the second photodetector 152 may not be one light-receiving element and may have a plurality of light-receiving elements.

In the first region A1, the sample 20 and the reagent L react with each other to generate a reactant that develops a specific color. The color of the first region A1 is changed by the generation of the reactant, and the change in the color appears as a change in the optical density of the first region A1. The first output light is output light corresponding to the optical density of the first region A1, and information on the reactant is reflected in the first output light by, for example, the absorption of light by the reactant. The optical density of the first region A1 changes depending on the amount of reactant, and the amount of reactant indicates the concentration of the substance to be tested in the sample 20. Therefore, it is possible to measure the concentration of the substance to be tested on the basis of the first detection signal indicating the first output light including the information on the reactant.

In contrast, in the second region A2, since there is no reagent L, no reactant is generated. Therefore, since the sample 20 is developed in the second region A2, the optical density changes depending on the influence of the sample 20 before and after the instillation of the sample 20. However, since no reactant is generated, the optical density is different from the optical density of the first region A1. The second output light is output light corresponding to the optical density of the second region A2 and does not include the information on the reactant.

As described above, the information on the reactant resulting from the substance to be tested is reflected in the first output light. In addition, information on the other substances is also reflected in the first output light. For example, in a case in which the sample 20 is blood, in addition to information on the substance to be tested included in the blood, information on the other substances is reflected in the first output light. Here, the information on the substances other than the reactant included in the first output light is also included in the second output light. Therefore, for example, it is possible to extract only the information on the reactant resulting from the substance to be tested by subtracting the information included in the second output light from the information included in the first output light.

The processor 170 acquires the first detection signal corresponding to the first output light and the second detection signal corresponding to the second output light and corrects the first detection signal on the basis of the second detection signal. For example, the processor 170 subtracts the second detection signal from the first detection signal to calculate the difference between the two signals or divides the first detection signal by the second detection signal to calculate a ratio between the two signals. The processor 170 derives the concentration of the substance to be tested on the basis of the first detection signal corrected in this way. That is, the processor 170 uses the second detection signal as a reference signal to be referred to as a reference and corrects the first detection signal, using the second detection signal as the reference signal.

The processor 170 includes, for example, a CPU and a memory, and the CPU executes a program to perform a process of deriving the concentration of the substance to be tested. In addition, the processor 170 controls the overall operation of each unit of the measurement unit 110.

In the example illustrated in FIG. 3, the first photodetector 151 is disposed at a position facing the opening 17D of the case 17 in the analysis chip 10 loaded on the loading unit 30. In addition, the first light source 141 is disposed at a position where the first detection light is emitted in an oblique direction with respect to the opening 17D. This layout of the first photodetector 151 and of the first light source 141 is an example, and various modifications can be made. For example, in a case in which a light guide member that guides the first detection light or the second output light between the opening 17D, and the first photodetector 151 and the first light source 141 is used, the first photodetector 151 and the first light source 141 can be moved to various positions. This is the same for the layout of the second photodetector 152 and of the second light source 142, and layouts other than that illustrated in FIG. 3 can be used.

Figure 4:
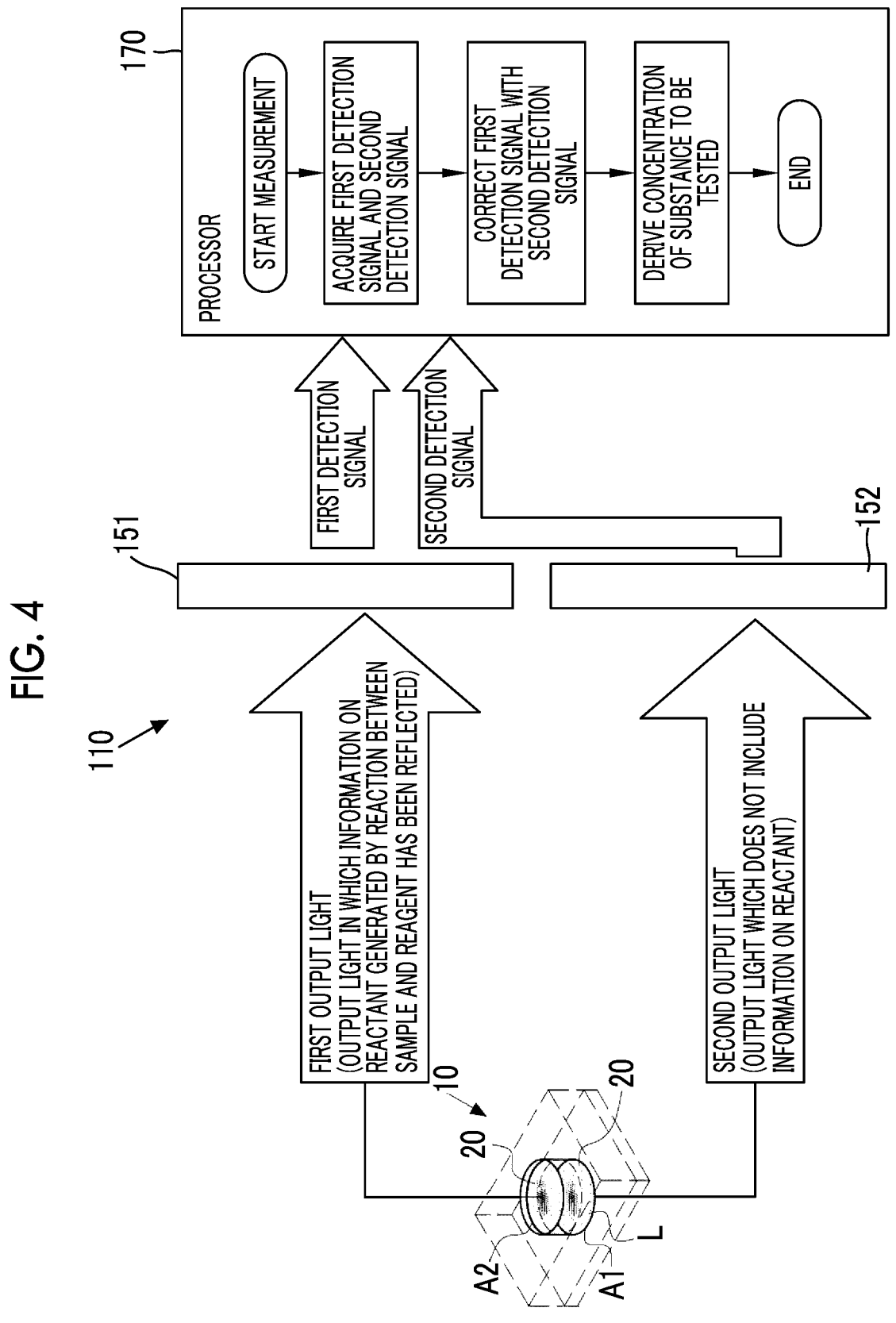
FIG. 4 is a summary diagram illustrating a process of the analysis device.

FIG. 4 illustrates a processing procedure of a measurement process of the measurement unit 110 of the analysis device 100 according to the first embodiment. First, the sample 20 is instilled into the analysis chip 10 by the dispensing mechanism P. The analysis chip 10 into which the sample 20 has been instilled is loaded on the measurement unit 110. The measurement unit 110 sequentially detects the first output light and the second output light using the loaded analysis chip 10. For example, after the analysis chip 10 is loaded, the measurement unit 110 turns on the first light source 141 to irradiate the first region A1 with the first detection light. In a case in which the first detection light is emitted, the first output light is output from the first region A1. The first photodetector 151 detects the first output light and outputs the first detection signal corresponding to the first output light. The processor 170 acquires the first detection signal.

Then, the measurement unit 110 turns on the second light source 142 such that the second light source 142 irradiates the second region A2 with the second detection light. In a case in which the second detection light is emitted, the second output light is output from the second region A2. The second photodetector 152 detects the second output light and outputs the second detection signal corresponding to the second output light. The processor 170 acquires the second detection signal.

As described above, the analysis device 100 uses the analysis chip 10 which has two regions of the first region A1 that has the reagent L reacting with the substance to be tested and the second region A2 that does not have the reagent L and in which the first region A1 is provided in the second surface 10B and the second region A2 is provided in the first surface 10A opposite to the second surface 10B. The analysis device 100 performs a step of irradiating the first region A1 of the analysis chip 10 with the first detection light from the second surface 10B using the first light source 141. In addition, the analysis device 100 performs a step of irradiating the second region A2 of the analysis chip 10 with the second detection light from the first surface 10A using the second light source 142. Then, the processor 170 performs a step of directing the first photodetector 151 to detect the first output light that is output from the first region A1 in a case in which the first light source 141 irradiates the analysis chip 10 with the first detection light and acquiring the first detection signal output by the first photodetector 151. In addition, the processor 170 performs a step of directing the second photodetector 152 to detect the second output light that is output from the second region A2 in a case in which the second light source 142 irradiates the analysis chip 10 with the second detection light and acquiring the second detection signal output by the second photodetector 152.

The first detection signal is a signal corresponding to the first output light in which the information on the reactant has been reflected, and the second detection signal is a signal corresponding to the second output light which does not include the information on the reactant. The processor 170 performs a step of correcting the first detection signal with the second detection signal and deriving the concentration of the substance to be tested on the basis of the corrected first detection signal. In this way, the process of measuring the concentration of the substance to be tested included in the sample 20 ends.

As described above, the processor 170 corrects the first detection signal including the information on the reactant, using the second detection signal that does not include the information on the reactant as the reference signal. Therefore, it is possible to remove the information on substances other than the reactant from the first detection signal. As a result, in a case in which the sample 20 is analyzed using the analysis chip, it is possible to measure the concentration of the substance to be tested in the sample 20 with higher accuracy than that in the related art. For example, in a case in which whole blood is used as the sample 20, the first detection signal is a signal including all of the information on substances other than the substance to be tested included in the whole blood, in addition to the information on the reactant. However, the use of the second detection signal that does not include the information on the reactant as the reference signal makes it possible to extract the information on only the substance to be tested from the first detection signal. Therefore, even in a case in which the analysis chip is used, it is possible to increase the accuracy of measuring the concentration as compared to the related art.

In addition, the analysis device 100 uses the analysis chip 10 that has one surface having the first region A1 provided therein and the other surface having the second region A2 provided thereon and comprises the first light source 141 and the first photodetector 151 for the first region A1 and the second light source 142 and the second photodetector 152 for the second region A2. Therefore, it is possible to detect the output light from each of the first region A1 and the second region A2, without changing the relative positional relationship between the analysis chip 10, and the light source and the photodetector. As a result, it is possible to shorten the processing time as compared to a case in which one set of the light source and the photodetector is used.

In this example, whole blood is described as an example of the sample 20. However, the sample 20 may be blood plasma or blood serum. The blood plasma or the blood serum also includes substances other than the substance to be tested. According to the technology of the present disclosure, it is possible to remove the information on substances other than the substance to be tested.

In addition, in this example, the wavelength ranges of the light emitted to the first region A1 and to the second region A2 are the same. However, the wavelength ranges may not be completely the same.

Further, in this example, the first photodetector 151 and the second photodetector 152 detect the first output light and the second output light at different times, respectively. Specifically, the irradiation time when the first light source 141 irradiates the first region A1 with the first detection light and the irradiation time when the second light source 142 irradiates the second region A2 with the second detection light are also different from each other. The mixture of the first output light and the second output light is suppressed by this configuration in which the first photodetector 151 and the second photodetector 152 detect light at different times. It is possible to reduce the mutual influence of the first detection signal and the second detection signal which causes noise. This makes it possible to further increase the accuracy of measuring the concentration.

Image Sensor

The example in which a photodiode is used as the first photodetector 151 has been described above. However, as illustrated in FIG. 5, an image sensor 151A having an imaging surface in which a plurality of light-receiving elements are two-dimensionally arranged may be used as the first photodetector 151. The following effects are obtained by this configuration.

In a case in which the sample 20 is developed in the first region A1 of the analysis chip 10, the area of a development region may change depending on the development state of the sample 20. In FIG. 5, in a development region D1 on a left side, the sample 20 is developed in substantially the entire first region A1 exposed through the opening 17D. On the other hand, in a development region D2 on a right side, the sample 20 is not developed in the entire first region A1. The development region D2 has a smaller area than the development region D1.

In this case, for example, a photodiode composed of a single light-receiving element does not have a spatial resolution for identifying the development region and the other regions. Therefore, the first detection signal output by the photodiode has a value obtained by averaging the optical densities of the development region and the other regions. Therefore, in a case in which the area of the development region is small, the optical density indicated by the first detection signal output from the photodiode is reduced due to the influence of a non-development region. For example, in the example illustrated in FIG. 5, a case is considered in which the optical densities of the development region D1 and the development region D2 are the same on the premise that the optical density of the development region D2 is higher than the optical density of the other regions. In this case, the amount of output light from the first region A1 on the right side in FIG. 5 which has the relatively small development region D2 is larger than the amount of output light from the first region A1 on the left side which has the relatively large development region D1 due to the influence of a region having a low optical density other than the development region D2.

In a case in which the image sensor 151A is used as the first photodetector 151 as illustrated in FIG. 5, it is possible to solve the above-mentioned problems. The image sensor 151A is, for example, a complementary metal oxide semiconductor (CMOS) image sensor or a charge coupled device (CCD) image sensor and has an imaging surface in which a plurality of light-receiving elements are two-dimensionally arranged. Therefore, the image sensor 151A has a spatial resolution unlike the photodiode. Therefore, the image sensor 151A can image the first region A1 to identify a development region D, such as the development regions D1 and D2, and the other regions.

The image sensor 151A can output a first region image 61 obtained by imaging the first region A1, such as a first region image 61A and a first region image 61B illustrated in FIG. 5, as the first detection signal. The processor 170 identifies the development region D in which the sample 20 has been developed and the other regions in the first region A1 on the basis of the first region image 61 and corrects the first detection signal according to the development region D. The processor 170 performs image analysis, such as contour extraction, on the basis of the first region image 61 to extract the development region D. Then, the processor 170 corrects the first detection signal indicating the optical density of the first region A1 according to the development region D. For example, in a case in which the processor 170 acquires the first region image 61A obtained by imaging the first region A1 including the development region D1 on the left side in FIG. 5 as the first region image 61, the optical density of the first region A1 is determined using the pixel values of the entire first region A1 since the entire first region A1 exposed through the opening 17D is the development region D1. On the other hand, in a case in which the processor 170 acquires the first region image 61B obtained by imaging the first region A1 including the development region D2 on the right side in FIG. 5, the optical density of the first region A1 is determined using the pixel values of only the development region D2 since a portion of the first region A1 is the development region D2.

As described above, the processor 170 identifies the development region D, in which the sample 20 has been developed, in the first region A1 on the basis of the first region image 61 acquired from the image sensor 151A and corrects the first detection signal according to the development region D. Therefore, even in a case in which the development region D is different, it is possible to accurately understand the optical density of the first region A1. As a result, it is possible to further increase the accuracy of measuring the concentration of the substance to be tested.

In FIG. 5, the example in which the first photodetector 151 is used to identify the development region D of the first region A1 has been described. The same applies to the second photodetector 152. That is, the second photodetector 152 may be an image sensor that has an imaging surface in which a plurality of light-receiving elements are two-dimensionally arranged, similarly to the image sensor 151A, and that can image the second region A2 and output a second region image (similarly to the first region image 61) obtained by imaging the second region A2 as the second detection signal. The processor 170 identifies the development region D, in which the sample 20 has been developed, in the second region A2 on the basis of the second region image and corrects the second detection signal according to the development region D. Therefore, even in a case in which the development region D of the sample 20 in the second region A2 is different, it is possible to accurately understand the optical density of the second region A2. As a result, it is possible to further increase the accuracy of measuring the concentration of the substance to be tested.

In addition, as described above, the wavelength range of the light emitted from the first light source 141 to the first region A1 includes a specific wavelength range that is determined according to at least one of the substance to be tested or the reagent.

Further, a light source that can emit light in a plurality of different wavelength ranges as the light in the specific wavelength range may be used as the first light source 141.

As the first light source 141 that can emit light in a plurality of wavelength ranges, a plurality of light sources that can emit light in different wavelength ranges may be combined. For example, a light source having a broad wavelength range, such as a halogen lamp, and a plurality of bandpass filters that pass light in different wavelength ranges may be combined to cut out light in different wavelength ranges.

The wavelength range of the light emitted by the second light source 142 is also determined according to the light emitted by the first light source 141. Therefore, similarly to the first light source 141, a light source that can emit light in a plurality of different wavelength ranges may be used as the second light source 142.

In addition, in the above-described embodiment, the example in which a dry reagent is used as the reagent L has been described. However, the reagent L may not be the dry reagent and may be a liquid reagent. Further, the reagent L may not be fixed in the carrier in a case in which the analysis chip is manufactured and may be instilled into the first region A1 by the dispensing mechanism P immediately before the measurement, similarly to the sample 20.

Furthermore, in the above-described embodiment, blood has been described as an example of the sample 20. However, the sample 20 may not be blood, and the technology of the present disclosure can be applied to a biological substance other than blood.

Further, in the above-described embodiment, the following various processors can be used as a hardware structure of the processor. The various processors include, for example, a CPU which is a general-purpose processor executing software (programs) to function as various processing units, a programmable logic device (PLD), such as a field-programmable gate array (FPGA), whose circuit configuration can be changed after manufacture, and a dedicated electric circuit, such as an application specific integrated circuit (ASIC), which is a processor having a dedicated circuit configuration designed to perform a specific process.

In addition, the above-described processes may be performed by one of the various processors or by a combination of two or more processors of the same type or different types (for example, a combination of a plurality of FPGAs and a combination of a CPU and an FPGA). Further, a plurality of processing units may be configured by one processor. An example in which a plurality of processing units are configured by one processor is an aspect in which a processor that implements the functions of the entire system including a plurality of processing units using one integrated circuit (IC) chip is used, such as a system-on-chip (SOC).

In addition, specifically, an electric circuit (circuitry) obtained by combining circuit elements, such as semiconductor elements, can be used as the hardware structure of these processors.

Further, the technology of the present disclosure is applied to a computer-readable storage medium (for example, a USB memory or a digital versatile disc (DVD)-read only memory (ROM)) that stores an operation program of the analysis device in a non-transitory manner, in addition to the operation program of the analysis device.

In addition, the above descriptions and illustrations are detailed descriptions of portions related to the technology of the present disclosure and are merely examples of the technology of the present disclosure. For example, the above description of the configurations, functions, operations, and effects is the description of examples of the configurations, functions, operations, and effects of portions according to the technology of the present disclosure. Therefore, it goes without saying that unnecessary portions may be deleted or new elements may be added or replaced in the above descriptions and illustrations without departing from the gist of the technology of the present disclosure. In addition, in the content described and illustrated above, the description of, for example, common technical knowledge that does not need to be particularly described to enable the implementation of the technology of the present disclosure is omitted in order to avoid confusion and to facilitate the understanding of portions related to the technology of the present disclosure.

All of the documents, the patent applications, and the technical standards described in the specification are incorporated by reference herein to the same extent as each individual document, each patent application, and each technical standard are specifically and individually stated to be incorporated by reference.

What is claimed is:

1. An analysis device that analyzes a sample including a substance to be tested and that uses an analysis chip that has two regions of a first region, which has a reagent reacting with the substance to be tested, and a second region, which does not have the reagent, and has a first surface in which the first region is provided and a second surface which is opposite to the first surface and in which the second region is provided, the analysis device comprising:

a first light source configured to irradiate the first region of the analysis chip with light from a first surface side;

a second light source configured to irradiate the second region of the analysis chip with light from a second surface side;

a first photodetector configured to detect a first output light which is output from the first region in a case in which the first light source irradiates the analysis chip with the light and that outputs a first detection signal corresponding to the first output light;

a second photodetector that configured to detect a second output light which is output from the second region in a case in which the second light source irradiates the analysis chip with the light and that outputs a second detection signal corresponding to the second output light; and a processor configured to acquire the first detection signal from the first photodetector, and configured to acquire the second detection signal from the second photodetector, and configured to correct the first detection signal with the second detection signal to derive a concentration of the substance to be tested.

2. The analysis device according to claim 1, wherein the first photodetector and the second photodetector detect the light at different times.

3. The analysis device according to claim 1, wherein the first photodetector is an image sensor that has an imaging surface in which a plurality of light-receiving elements are two-dimensionally arranged and that is capable of imaging the first region and outputting a first region image obtained by imaging the first region as the first detection signal, and the processor identifies a development region in which the sample has been developed in the first region on the basis of the first region image and corrects the first detection signal according to the development region.

4. The analysis device according to claim 1, wherein the second photodetector is an image sensor that has an imaging surface in which a plurality of light-receiving elements are two-dimensionally arranged and that is capable of imaging the second region and outputting a second region image obtained by imaging the second region as the second detection signal, and the processor identifies a development region in which the sample has been developed in the second region on the basis of the second region image and corrects the second detection signal according to the development region.

5. The analysis device according to claim 1, wherein a wavelength range of the light emitted from the first light source and from the second light source includes light in a specific wavelength range that is determined according to at least one of the substance to be tested or the reagent.

6. The analysis device according to claim 5, wherein the first light source and the second light source are capable of emitting light in a plurality of different wavelength ranges as the light in the specific wavelength range.

7. The analysis device according to claim 1, wherein the reagent is a dry reagent.

8. The analysis device according to claim 1, wherein the sample is whole blood, and the substance to be tested is a specific substance included in blood plasma or in blood serum.

9. An analysis method for analyzing a sample including a substance to be tested, an analysis chip, which has two regions of a first region and a second region and has a first surface and a second surface opposite to the first surface, being used, the first region having a reagent reacting with the substance to be tested, the second region not having the reagent, the first region being provided in the first surface, and the second region being provided in the second surface, the analysis method comprising:

a step of irradiating the first region of the analysis chip with light from a first surface side with a first light source;

a step of irradiating the second region of the analysis chip with light from a second surface side with a second light source;

a step of causing a first photodetector to detect a first output light which is output from the first region in a case in which the first light source irradiates the analysis chip with the light and acquiring a first detection signal output by the first photodetector;

a step of causing a second photodetector to detect a second output light which is output from the second region in a case in which the second light source irradiates the analysis chip with the light and acquiring a second detection signal output by the second photodetector; and a step of acquiring the first detection signal, acquiring the second detection signal, and correcting the first detection signal with the second detection signal to derive a concentration of the substance to be tested.

* * * * *